United States Patent [19]

Griffiths

[11] Patent Number: 5,128,119
[45] Date of Patent: Jul. 7, 1992

[54] METHODS FOR TECHNETIUM/RHENIUM LABELING OF F(AB¹)₂ FRAGMENTS

[75] Inventor: Gary L. Griffiths, Morristown, N.J.

[73] Assignee: Immunomedics, Inc., Warren, N.J.

[21] Appl. No.: 392,280

[22] Filed: Aug. 10, 1989

Related U.S. Application Data

[63] Continuation-in-part of Ser. No. 364,373, Jun. 12, 1989, abandoned.

[51] Int. Cl.⁵ .................... A61K 43/00; A61K 49/02; C07B 59/00
[52] U.S. Cl. .................................... 424/1.1; 530/402; 530/408; 530/391.5; 530/391.3; 534/14; 436/804; 435/975; 424/9
[58] Field of Search ................. 424/1.1; 530/389, 390, 530/402, 408; 436/804; 435/975

[56] References Cited

U.S. PATENT DOCUMENTS

| | | | |
|---|---|---|---|
| Re. 32,417 | 5/1987 | Burchiel | 424/1.1 |
| 3,725,295 | 4/1973 | Eckelman et al. | 252/301.1 R |
| 4,057,617 | 11/1977 | Abramovici et al. | 424/1 |
| 4,293,537 | 10/1981 | Wong | 424/1 |
| 4,401,647 | 8/1983 | Krohn et al. | 424/1.1 X |
| 4,472,371 | 9/1984 | Burchiel et al. | 424/1.1 |
| 4,478,815 | 10/1984 | Burchiel et al. | 424/1.1 |
| 4,500,507 | 2/1985 | Wong | 424/1.1 |
| 4,877,868 | 10/1989 | Reno et al. | 530/390 |
| 5,053,493 | 10/1991 | Pak et al. | 530/402 |
| 5,061,641 | 10/1991 | Shochat et al. | 424/1.1 X |
| 5,078,985 | 1/1992 | Rhodes | 424/1.1 |

FOREIGN PATENT DOCUMENTS

| | | |
|---|---|---|
| 0005638 | 11/1979 | European Pat. Off. . |
| 0106608 | 4/1984 | European Pat. Off. . |
| 0336678 | 10/1989 | European Pat. Off. . |
| 88/07382 | 10/1988 | PCT Int'l Appl. . |

Primary Examiner—Robert L. Stoll
Assistant Examiner—John M. Covert
Attorney, Agent, or Firm—Foley & Lardner

[57] ABSTRACT

A method for radiolabeling a protein with a radioisotope of technetium of rhenium comprises the steps of contacting a solution of a protein containing a plurality of adjacent free sulfhydryl groups, or in particular cases, intact protein containing at least one disulfide group, with stannous ions, and then with radiopertechnetate or radioperrhenate, the amount of stannous ion being sufficient to substantially completely reduce the radiopertechnetate or radioperrhenate, and recovering radiolabeled protein.

48 Claims, No Drawings

METHODS FOR TECHNETIUM/RHENIUM LABELING OF F(AB¹)₂ FRAGMENTS

REFERENCE TO RELATED APPLICATION

This application is a Continuation-in-Part of U.S. patent application Ser. No. 07/364,373, filed Jun. 12, 1989 now abandoned.

BACKGROUND OF THE INVENTION

The present invention relates to improved and optimized methods for direct labeling of proteins, especially antibodies and/or antibody fragments, with radioisotopes of technetium and rhenium.

The isotope Technetium-99m is among the most valuable in diagnostic nuclear medicine due to its ready availability, low cost and favorable radiochemical characteristics. It is used widely as an agent for labeling macromolecules such as monoclonal antibodies and can be bound to the protein in various ways. Early work mainly used the bifunctional chelate approach, i.e., use of a chelator which contained another functional group for linkage to the protein. Various forms of diethylenetriaminepentaacetic acid (DTPA) were used, for example, to bind to the antibody and also to chelate the radiometal ion.

Direct labeling of protein was also tried, using a "pretinning" protocol, requiring severe conditions and long "pretinning" times, but radiolabeling at 100% incorporation was not achieved. Moreover, the presence of extremely high amounts of stannous ion for long periods compromised the immunoreactivity of the antibody. The process also generally necessitated a post-labeling purification column. Attempts to repeat pretinning procedures of others with F(ab')₂ antibody fragments were unsatisfactory in achieving Tc-99m labeling.

Other, more recent direct labeling methods have required separate vials, one for antibody and one for stannous ion complexed to a transchelator such as a phosphate and/or phosphonate.

The element below technetium in the periodic table, rhenium, has similar chemical properties and might be expected to react in an analogous manner to technetium. There are some 34 isotopes of rhenium and two of them in particular, rhenium-186 (t ½, 90h; gamma 137 keV, beta 1.07, 0.93 MeV) and rhenium-188 (t ½, 17h; gamma 155 keV, beta 2.12 MeV), are prime candidates for radioimmunotherapy using monoclonal antibody approaches. Both isotopes also have gamma emissions at suitable energies for gamma camera imaging purposes. Rhenium-186 is obtained from reactor facilities by bombardment of enriched rhenium-185 with neutrons, which yields rhenium-186 in a "carrier-added" form containing a large excess of non-radioactive rhenium-185. Rhenium-188 is obtained from a tungsten-188/rhenium-188 generator (Oak Ridge National Laboratory) and can be eluted from the generator in a substantially carrier-free form with little tungsten breakthrough. Also, the energy deposition from this isotope at a high $\Delta = 1.63$ g-rad/$\mu$Ci-h is close to another potently energetic potential therapeutic, yttrium-90 ($\Delta = 1.99$ g-rad/$\mu$Ci-h) while at the same time the chemical properties of rhenium may make it less of a bone-seeking agent than yttrium (which is often contaminated with strontium-90) and give rise to better tumor/organ biodistribution and dosimetry.

Although many groups have alluded to the possibility of utilizing rhenium to label antibodies in the same fashion as technetium, little successful work has been published. Low rhenium incorporations are usually seen with antibody-chelate conjugates and there is a general tendency of rhenium to reoxidize back to perrhenate and then dissociate from complexation. Besides, use of the bifunctional chelate approach often requires an organic synthesis with a lengthy series of intermediates to be isolated and purified prior to antibody conjugation.

Numerous attempts by the inventor and others to produce a F(ab)'₂ fragment radiolabeled with technetium or rhenium, and substantially free of Fab' fragments were unsuccessful. Such a conjugate is desirable for its advantageous combination of clearance rate, extent of tumor localisation and biodistribution.

A need continues to exist for simple, efficient methods for radiolabeling proteins with radioisotopes of technetium and rhenium.

OBJECTS OF THE INVENTION

One object of the present invention is to readily produce a highly immunoreactive technetium or rhenium radiolabeled antibody or antibody fragment, particularly including a F(ab')₂ fragment, which is stable to loss of label by transchelation or reoxidation.

Another object of the invention is to provide a method for direct radiolabeling of a protein which produces high yields of labeled product with minimal contamination with by-products.

Another object of the invention is to provide a convenient and efficient radiolabeling kit for use in introducing technetium or rhenium radioisotope into an antibody or antibody fragment.

Upon further study of the specification and appended claims, further objects and advantages of this invention will become apparent to those skilled in the art.

SUMMARY OF THE INVENTION

The foregoing objectives are achieved by providing a method for radiolabeling a protein containing a plurality of spatially adjacent free sulfhydryl groups with a radioisotope of technetium or rhenium, comprising the steps of contacting a solution of said protein containing a plurality of spatially adjacent free sulfhydryl groups with stannous ions, and then with radiopertechnetate or radioperrhenate, the amount of stannous ion being in slight excess in the case of technetium and in greater excess in the case of rhenium over that required to substantially completely reduce said radiopertechnetate or radioperrhenate, and recovering radiolabeled protein.

The invention also provides technetium or rhenium radiolabeling kits for effecting the labeling process of the invention, especially for producing Tc-99m and rhenium radiolabeled antibodies and antibody fragments, and improved methods of radioantibody imaging and therapy using antibodies and antibody fragments radioalabeled according to the invention.

DETAILED DESCRIPTION

It has now been found that a protein, in particular an antibody or antibody fragment, having a plurality of spatially adjacent free sulfhydryl groups can selectively bind technetium and rhenium radiometal ions, under mild conditions, to form tight bonds to the sulfhydryl groups that are quite stable in blood and other bodily fluids and tissues. Both the reagents and the conditions in the present method are greatly simplified, but the method is particularly adapted for technetium or rhenium labeling and it is surprisingly and unexpectedly shown that optimal conditions for introducing each label are different.

The present method broadly comprises the step of contacting a solution of a protein containing a plurality of spatially adjacent free sulfhydryl groups, said solution also containing tin(II) ions, with a solution of Tc-99m-pertechnetate or perrhenate (using a radioisotope of rhenium of therapeutic or imaging utility) ions, whereby a solution of technetium or rhenium radiolabeled protein is obtained. The procedure is simple and practical for the nuclear medicine physician and technologist. Preferred embodiments include applying the method of the invention to produce radiolabeled antibodies or antibody fragments useful for gamma imaging and radioisotope therapy.

The labeling method and kit of the invention may be used to bind radioiosotopes of technetium and rhenium to other proteins with the requisite free sulfhydryl groups. Proteins which contain two or more proximal free sulfhydryl groups can be labeled directly. Those which contain disulfide groups, normally linked through a cystine residue, can be treated with a reducing agent to generate the free sulfhydryl groups. This may result in fragmentation of the protein if the disulfide bond links polypeptide chains which are not continuous, or it may merely result in chain separation, possibly involving a change in conformation of the protein if the disulfide bond joins remote segments of a single polypeptide chain. Sulfhydryl groups can be introduced into a polypeptide chain to provide the requisite proximal groups. Use of Traut's Reagent (iminothiolane) for this purpose is not preferred, whereas use of oligopeptides containing several adjacent sulfhydryl groups is efficacious. In particular, use of metallothionein or, preferably, its C-terminal hexapeptide fragment (hereinafter, "MCTP"), results in significant improvement.

Reduction of an antibody or F(ab')$_2$ fragment with known disulfide bond reducing agents, e.g., dithiothreitol, cysteine, mercaptoethanol and the like, gives after a short time, typically less than one hour, including purification, antibody having from 1-10 free sulfhydryl groups by analysis. When labeled with technetium using a reducing agent such as stannous ion under the present conditions, 100% incorporation of Tc-99m to protein is seen together with >95% retention of immunoreactivity.

It has been found that attempts to achieve partial reduction of F(ab')$_2$ resulting from enzymatic cleavage of intact antibody often result in considerable further cleavage to Fab', and that even later attempts to reduce pertechnetate or perrhenate with stannous ion, in the presence of F(ab')$_2$, are accompanied by disulfide bond reduction and further cleavage to Fab', resulting in some label being lost to the monovalent fragment. For improved production of F(ab')$_2$ antibody fragments, substantially free of further Fab' cleavage products, it has surprisingly and unexpectedly been found that cleavage to F(ab')$_2$ fragments of antibody already having free proximal sulfhydryl groups thereon, followed by labeling with reduced pertechnetate or perrhenate, results in highly efficient labeling of the F(ab')$_2$ with substantially no further cleavage to Fab, The F(ab')$_2$-SH can be produced by partial reduction of intact antibody as described above or by introduction of free sulfhydryl groups into intact antibody, e.g., by conjugation with activated MCTP or an equivalent polythiol addend, followed by cleavage, preferably enzymatically with, e.g. pepsin, under conventional, preferably acidic, conditions and in the absence of oxygen, to form the sulfhydryl-containing bivalent fragment.

Much less tin(II) is needed to achieve 100% Tc-99m incorporation than was previously thought. The general amount of tin used for labeling compounds with Tc in most prior art methods is about 100-200 micrograms per milligram of protein. However, because of the great binding power of the sterically close SH groups and the subnanogram quantities of TcO$_4^-$ that normally must be reduced to obtain adequate activity for gamma imaging, much less tin(II) can be effectively used. Reduction is effected by stannous ion, generally in aqueous solution. It will be appreciated that stannous ion can be generated in situ from tin metal, e.g., foil, granules, powder, turnings and the like, by contact with aqueous acid, e.g., HCl, and is usually added in the form of SnCl$_2$, advantageously in a solution that is also about 0.1 mM in HCl.

In general, it is advantageous to work with a concentration of antibody or antibody fragment of about 0.01-10 mg per ml, preferably about 0.1-5 mg/ml, of solution, generally in saline, preferably buffered to a mildly acidic pH of about 4.0-4.5. In such case, the amount of stannous ion needed for reduction of a normal imaging activity of pertechnetate is about 0.1-50 $\mu$g/ml, preferably about 0.5-25 $\mu$g/ml, in proportion to the amount of protein.

When labeling the foregoing quantity of antibody or antibody fragment, the amount of pertechnetate is generally about 2-50 mCi/mg of antibody or antibody fragment, and the time of reaction is about 0.1-10 min. With the preferred concentrations of protein and stannous ions noted above, the amount of pertechnetate is preferably about 5-30 mCi/mg, and the time of reaction is preferably about 1-5 min.

Pertechnetate is generally obtained from a commercially available generator, most commonly in the form of NaTcO$_4$, normally in saline solution. Other forms of pertechnetate may be used, with appropriate modification of the procedure, as would be suggested by the supplier of a new form of generator or as would be apparent to the ordinary skilled artisan. Pertechnetate is generally used at an activity of about 0.2-10 mCi/ml in saline, e.g., 0.9% ("physiological") saline, buffered at a pH of about 3-7, preferably 3.5-5.5, more preferably about 4.5-5.0. Suitable buffers include, e.g., acetate, tartrate, citrate, phosphate and the like.

The reduction is normally effected under an inert gas atmosphere, e.g., nitrogen, argon or the like. The reaction temperature is generally maintained at about room temperature, e.g., 18°-25° C.

These conditions routinely result in substantiantially quantitative incorporation of the label into the protein in a form which is highly stable to oxidation and resistant to transchelation in saline and serum. For example, it is now possible to consistently label IgG, previously reduced with a thiol-generating reagent, with from 0.5 to 5 micrograms of Sn(II) per milligram of IgG, in essentially quantitative yield. Generally, at least about 95% of the label remains bound to protein after standing overnight at 37° C. in serum. Furthermore the immunoreactivity of this protein is hardly reduced after this serum incubation, showing that the conjugates are still completely viable imaging agents out to at least 24 hours.

At these concentrations, no transchelator such as phosphonate, tartrate, glucoheptonate or other well known Sn(II) chelating agent is required to keep the tin in solution. Sn(II) compounds such as stannous chloride and stannous acetate have been used successfully in these experiments. Other readily available and conventional Sn(II) salts are also effective. There are only three essential ingredients; the reduced antibody, the aqueous stannous ion and the pertechnetate solution. Under the conditions described hereunder, 100% of Tc-99m incorporation into intact antibody and Fab/Fab' fragments can be readily achieved. In the case of F(ab')$_2$, the labeling conditions result in 100% incorporation of Tc-99m, but also produce a certain amount of radiolabeled Fab' in addition to radiolabeled F(ab')$_2$. The improvement set forth hereinabove for producing radiolabeled F(ab')$_2$ obviate this problem.

The resultant Tc-99m-radiolabeled antibodies and antibody fragments are suitable for use in scintigraphic imaging of, e.g., tumors, infectious lesions, microorganisms, clots, myocardial infarctions, atherosclerotic plaque, or normal organs and tissues. Such imaging methods are well known in the art. The radioantibody solutions as prepared above are ready for immediate injection, if done in a properly sterilized, pyrogen-free vial. Also, no blocking of free sulfhydryl groups after technetium binding is necessary for stabilization.

The method of the invention is particularly attractive for labeling antibodies and antibody fragments, although proteins such as albumin, drugs, cytokines, enzymes, hormones, immune modulators, receptor proteins and the like may also be labeled. Antibodies contain one or more disulfide bonds which link the heavy chains, as well as disulfide bonds which join light and heavy chains together. The latter disulfide bonds are normally less accessible to disulfide reducing agents and the bonds linking heavy chains can normally be selectively cleaved. The resultant fragments retain their immunospecificity and ability to bind to antigen. It will be understood that reduction of disulfide bonds linking the heavy chains of an immunoglobulin must be effected with care, since the normally less reactive disulfide bonds linking light and heavy chains will eventually be reduced if reducing conditions are too drastic or the reducing agent is left in contact with the fragments for too long a time.

Once reduced, the antibody-SH moieties are quite stable if stored under rigorously oxygen-free conditions. Stability is also increased with storage at lower pH, particularly below pH 6. It has been found that rapid cooling to the temperature of liquid nitrogen of antibodies and antibody fragments containing a plurality of free sulfhydryl groups permits storage thereof for prolonged periods of time without deterioration or significant loss of sulfhydryl groups. It is believed that bathing the tubes containing the antibody-SH or fragment-SH species in an atmosphere of nitrogen adds to the protection of low temperature and effectively prevents reoxidation of sulfhydryl groups to disulfides.

It will also be understood that the antibodies or antibody fragments to be radiolabeled can be antibodies which bind to antigens which include but are not limited to antigens produced by or associated with tumors, infectious lesions, microorganisms, parasites, myocardial infarctions, clots, atherosclerotic plaque, or normal organs or tissues.

By "antibodies and antibody fragments" is meant generally immunoglobulins that specifically bind to antigens to form immune complexes. The terms include conventional IgG, IgA, IgE, IgM, and the like, conventional enzyme digestion products such as F(ab')$_2$ fragments obtained by pepsin digestion of intact immunoglobulins, Fab fragments obtained by papain digestion of intact immunoglobulins, conventional monovalent Fab' and light-heavy chain fragments obtained by disulfide bond cleavage of F(ab')$_2$ fragments and intact antibody, respectively, as well as products having substantially similar properties to such immunoglobulins and fragments. Such similar proteins include antibody subfragments made by further digestion or manipulation of larger fragments, genetically engineered antibodies and/or fragments, and synthetic proteins having an antigen recognition domain which specifically binds to an antigen in a substantially analogous fashion to a "classical" immunoglobulin. The only substantive requirement for such a protein is that it have two or more proximal sulfhydryl groups to serve as chelators for the reduced pertechnetate or reduced perrhenate radiometal ion, by virtue of partial reduction or of introduction of polythiol moieties.

By "reduced pertechnate" or "reduced perrhenate" is meant the species of technetium or rhenium ion formed by stannous ion reduction of pertechneate or perrhenate and chelated by the thiol group(s). It is generally thought that reduced pertechnetate is in the form of Tc(III) and/or Tc(IV) and/or Tc(V) in such chelates, and that reduced perrhenate is in the form of Re(III) and/or Re(IV) and/or Re(V), but higher or lower oxidation states and/or multiple oxidation states cannot be excluded and are within the scope of the invention.

Rhenium is found just below technetium in the periodic table, has the same outer shell electronic configuration, and therefore might be expected to have very similar chemical properties, especially the behavior of analogous compounds. In fact, rhenium compounds qualitatively behave similarly to technetium compounds insofar as reduction and chelation are concerned but their reaction rates are quite different and they are dissimilar in certain important respects.

The radioisotope Re-186 is attractive for therapy and can also be used for imaging. It has a half-life of about 3.7 days, a high LET beta emission (1.07 MeV) and a convenient gamma emission energy (0.137 MeV). By analogy to technetium, rhenium is produced from perrhenate, and the reduced rhenium ions can bind nonspecifically to protein. Accordingly, a method for Re-186 labeling of proteins, wherein the reduced perrhenate is bound to sulfhydryl groups of a protein molecule such as an antibody, would be advantageous. Re-188 is a generator-produced beta and gamma emitter with a half-life of about 17 hours and is suitable for imaging and therapy. The development of commercial generators for rhenium-188 is currently underway; and in a preferred scenario, carrier free rhenium-188 is added directly to a vial containing stannous ion and IgG, to produce a rhenium radiolabeled protein which is ready for use in less than two hours. The half-life of rhenium-188, at 17 hours, makes speed of preparation particularly important.

The procedure is modified somewhat in the case of rhenium from that used with pertechnetate. In contrast to Tc-99m labeling procedures, perrhenate does not label reduced antibodies when low amounts of stannous ion reducing agent and short reactions times are used. However, by the use of higher amounts of stannous ion, e.g., stannous tartrate, and longer reaction times, thiol-reduced antibodies are successfully labeled with rhenium.

By judicious manipulation of conditions, better than 80% rhenium incorporations into antibody can be achieved in just a few hours, which is particularly important for rhenium-188 with its 17 hour half-life and potential for radiobiologic damage to the antibody. Labeling procedures are simpler than those currently required for iodine-131 radiolabeling and much simpler than what is currently required for labeling antibodies with yttrium-90 and copper-67. The short labeling time ensures retention of antibody immunoreactivity.

Conditions will vary depending upon whether the perrhenate is substantially carrier-free (e.g., generator-produced Re-188) or carrier-added (e.g., reactor-produced Re-186), the latter requiring more perrhenate for equivalent activity, and therefore more stannous ion reducing agent, although not necessarily more protein. This is an aspect not treated in the prior art.

Generally, a protein, preferably an antibody or antibody fragment, containing a plurality of adjacent/proximal sulfhydryl groups, will be used in concentrations reflecting the preferred therapy application of radioisotopes of rhenium. The types of protein that can be labeled and the definitions of antibodies and antibody fragment disclosed for technetium labeling are also valid for rhenium radiolabeling.

Labeling with substantially carrier-free Re-188-NaReO$_4$, the form which would normally be produced from a generator, is advantageously effected with the sulfhydryl-containing protein, e.g., antibody or fragment, at a protein concentration of about 1–20 mg/ml, preferably 10–20 mg/ml, in substantially the same solutions and under substantially the same conditions as pertechnetate. The amount of stannous ion used is generally about 100–10,000 $\mu$g/ml, preferably about 500–5,000 $\mu$g/ml, and preferably in proportion to the amount of protein. Using the foregoing amounts of protein and stannous ion, it is advantageous to use about 10–500 mCi, preferably about 50–250 mCi of substantially carrier-free Re-188-perrhenate, preferably again in proportion to the amount of protein. The reaction time is advantageously about 1 min to 4 hr, preferably about 15 min to 2 hr. Surprisingly and unexpectedly, the reagent ratios and reactions times that were optimal for pertechnetate labeling were not effective for perrhenate, and vice-versa.

Labeling with carrier-added Re-186-NaReO$_4$, the form which would normally be produced from a reactor and which generally contains about a 100- to 1,000-fold excess of Re-185 as carrier, is advantageously effected with the sulfhydryl-containing protein, e.g., antibody or fragment, at a protein concentration of about 1–20 mg/ml, preferably 10–20 mg/ml, in substantially the same solutions and under substantially the same conditions as for Re-188-perrhenate. However, because of the large amount of carrier, the amount of stannous ion used is generally about 1–1,000 mg/ml, preferably about 5–500 mg/ml, and preferably again in proportion to the amount of protein. Approximately the same activity of rhenium radioisotope and about the same reaction times are used for this isotope.

A short column procedure will normally suffice to remove any unbound rhenium and after this time it is ready for immediate injection, if done in a properly sterilized, pyrogen-free vial. Again, no blocking of free sulfhydryl groups after rhenium labeling is necessary for stabilization.

In a surprising and unexpected development, it has now been shown that proteins containing at least one disulfide group, e.g., intact antibodies (without prior reduction) can be simply and directly radiolabeled with rhenium using a larger amount of stannous ion to concommitantly reduce and bind together the antibody and the rhenium species. The "pretinning" procedures described elsewhere and earlier technetium-IgG labeling procedures gave poor results. Long and/or severe reactions are incompatible with the successful generation of an IgG-rhenium injectible.

In general, the concentration of unreduced protein, e.g., antibody, the reaction times, perrhenate activities and other conditions will be substantially the same as for Re-186 or Re-188 labeling of sulfhydryl-containing proteins, except that a larger amount of stannous ion is used. When the radioisotope in the radioperrhenate is substantially carrier-free Re-188, the concentration of antibody or antibody fragment in the solution is advantageously about 1–20 mg/ml, preferably about 10–20 mg/ml, and the amount of stannous ion is about 500–10,000 $\mu$g/ml, preferably about 500–5,000 $\mu$g/ml. When the radioisotope in the radioperrhenate is carrier-added Re-186, at the same concentration of antibody or antibody fragment, the amount of stannous ion is about 5–1,000 mg/ml, preferably about 50–500 mg/ml.

In fact, unmodified, unreduced IgG has been taken, placed in a vial with a stannous reductant and successfully labeled with perrhenate in as little as 45 minutes at room temperature. No pretinning is used, but perrhenate is added directly after the antibody and tin are mixed. The key is to have sufficient tin to effect a rapid reduction. A short separatory column, simpler in ease of operation than a typical iodine-131 label purification, gives a pure rhenium-IgG conjugate ready for injection.

Exposure of IgG to the conditions used does not impair its immunoreactivity as measured on an affinity column of bound antigen. It appears that an in situ reduction of protein disulfide groups by the stannous ion accompanies the perrhenate reduction and creates the necessary conditions for protein-metal complex formation. The fact that pertechnetate labels IgG much less favorably under the same conditions suggests this as a particularly novel and efficient route for obtaining rhenium antibodies with minimal manipulation.

Rhenium labeling is effected in substantially the same manner as technetium labeling, with special care being taken to insure the absence of air or oxygen in the system. The rhenium-labeled proteins prepared according to the invention show no sign of the ready reoxidation to perrhenate seen by other workers, indicating that the present method is not only facile but also stable. Coupled with this are the facts that much less IgG manipulation is needed for the present method, that Re-188 is available in a convenient generator format (with a single generator capable of daily use for a period of sixty days or more) and that no problems are encountered with strontium contamination, making rhenium-radiolabeled IgG an attractive therapeutic agent.

Rhenium antibody conjugates produced by these methods have been shown to be very stable, even when exposed in solution to the atmosphere for up to 5 days at least. This long term stability is important in an immunoradiotherapeutic as is retention of immunoreactivity during labeling procedures, which also has been demonstrated.

It must be recognized that the present approach is quite different from prior art approaches, due to the simplicity, effectiveness, efficiency and lack of major manipulation in the process as well as the stability of the rhenium conjugates. It is again emphasized that the relatively higher amount of tin and longer reaction times are not conducive to efficient pertechnetate labeling but are optimal for perrhenate, whereas the low tin, fast labeling conditions optimal for pertechnetate do not work for perrhenate. In particular, for about 1 mg of antibody, and an imaging activity of Tc-99m, very low tin and 5 min reaction times result in excellent results, whereas for therapy levels of Re-186 or Re-188 label, more than 500 µg/ml stannous ion is desirable, especially if intact antibody is used, and reaction times on the order of close to an hour are effective.

A kit for use in radiolabeling a protein, e.g., a Fab'-SH or F(ab')$_2$ fragment, or an intact antibody, with Tc-99m, using generator-produced pertechnetate, would include about 0.01–10 mg per unit dose of an antibody or antibody fragment which specifically binds an antigen associated with a tumor, an infectious lesion, a microorganism, a myocardial infarction, a clot, atherosclerotic plaque, or a normal organ or tissue, and which contains a plurality of adjacent free sulfhydryl groups; and about 0.1–50 µg per unit dose of stannous ions. The constituents of the kit are combined just prior to use with about 2–50 mCi of Tc-99m pertechnetate per mg of antibody or antibody fragment. The antibody/fragment-SH and the Sn(II) reducing agent are advantageously combined in a single solution in a vial which can be stored, e.g., in a liquid nitrogen bath, or lyophilized, preferably with added sugar as is well known in the art, prior to addition of the pertechnetate.

A kit for radiolabeling an antibody or antibody fragment with the Re-188 radioisotope of rhenium would typically include about 1–20 mg per unit dose of an antibody or antibody fragment which specifically binds an antigen associated with a tumor or an infectious lesion, and which contains a plurality of adjacent free sulfhydryl groups; and about 100–10,000 µg per unit dose of stannous ions; and would be combined just prior to use with about 10–500 mCi of substantially carrier-free Re-188 perrhenate per mg of antibody or antibody fragment. Advantageously, the kit constituents would be present in a single vial and stored or lyophilized as noted above until use for labeling.

A kit for radiolabeling an antibody or antibody fragment with the Re-186 radioisotope of rhenium would typically include about 1–20 mg per unit dose of an antibody or antibody fragment which specifically binds an antigen associated with a tumor or an infectious lesion, and which contains a plurality of adjacent free sulfhydryl groups; and about 1–1,000 mg per unit dose of stannous ions; and would be combined just prior to use with about 10–500 mCi of carrier-added Re-186 perrhenate per mg of antibody or antibody fragment. Single vial storage and use as above are preferred.

A kit for labeling unreduced intact antibody with either rhenium isotope would be similar to the foregoing, except for the larger amount of stannous ions generally used to reduce some of the disulfide bonds in the antibody as well as reducing the perrhenate.

The proteins in such kits are advantageously frozen or lyophilized, in sterile containers, and under an inert gas atmosphere, advantageously cooled and stored in a liquid nitrogen bath and gently thawed just prior to use. The kits are conveniently supplemented with sterile vials of buffers, saline, syringes, filters, columns and the like auxiliaries to facilitate preparation of injectable preparations ready for use by the clinician or technologist.

Variations and modifications of these kits will be readily apparent to the ordinary skilled artisan, as a function of the individual needs of the patient or treatment regimen, as well as of variations in the form in which the radioisotopes may be provided or may become available.

It will also be apparent to one of ordinary skill that the radiolabeled proteins, especially antibodies and antibody fragments, prepared according to the method of the invention, will be suitable, and in fact particularly convenient and efficacious, in methods of non-invasive scintigraphic imaging and for radioantibody therapy of tumors and lesions. In particular, in a method of imaging a tumor, an infectious lesion, a myocardial infarction, a clot, atherosclerotic plaque, or a normal organ or tissue, wherein an antibody or antibody fragment which specifically binds to an antigen produced by or associated with said tumor, infectious lesion, myocardial infarction, clot, atherosclerotic plaque, or normal organ or tissue, and radiolabeled with a pharmaceutically inert radioisotope capable of external detection, is parenterally injected into a human patient and, after a sufficient time for the radiolabeled antibody or antibody fragment to localize and for non-target background to clear, the site or sites of accretion of the radiolabeled antibody or antibody fragment are detected by an external imaging camera, it will be an improvement to use as the radiolabeled antibody or antibody fragment a Tc-99m-labeled antibody or antibody fragment made according to the method of the present invention.

Moreover, in a method of radioantibody therapy of a patient suffering from a tumor or an infectious lesion, wherein an antibody or antibody fragment which specifically binds to an antigen produced by or associated with a tumor or an infectious lesion, and radiolabeled with a therapeutically effective radioisotope, is parenterally injected into a human patient suffering from such tumor or infectious lesion, it will represent an improvement to use as the radiolabeled antibody or antibody fragment a rhenium radiolabeled antibody or antibody fragment made according to the method of the present invention, either from pre-reduced or unreduced antibody.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, all temperatures are set forth uncorrected in degrees Celsius;

EXAMPLE 1

Antibody reduction (a) In a typical run, a solution of 5 mg of purified monoclonal anti-CEA IgG (antibody which specifically binds to carcinoembryonic antigen, a marker associated with colorectal cancer) in 1 ml of phosphate-buffered saline (PBS), at a pH adjusted to 6.2–6.6, is made 30–50 millimolar in 2-mercaptoethanol. After standing at room temperature for 30–40 minutes, the sample is purified on an acrylamide column with deoxygenated acetate as buffer. The reduced IgG solution is concentrated to 1–2 mg/ml on Centricon and is analyzed for SH groups per IgG by the Ellman reaction. It is stored sterile filtered at 4° C. for convenience or frozen for greater stability of the SH groups.

EXAMPLE 2

Tc-99m Radiolabeling

In a typical run, a solution containing 125 nanograms of Sn(II) is mixed with a solution containing $3.6 \times 10^{-10}$ moles of monoclonal anti-CEA with free sulfhydryl groups, prepared according to Example 1 and having 1.2 SH per IgG by the Ellman reaction, giving a 2.9:1 ratio of Sn(II) to IgG. Addition of 2 mCi of technetium-99m as pertechnetate in saline, followed by incubation for 5 minutes at room temperature, gives a 100% incorporation of technetium into the protein as measured by HPLC and less than 1% pertechnetate remaining by ITLC in two different elution buffers. Immunoreactivity is >98% when measured on a CEA column. The solution of labeled antibody can be used directly for in vivo injection.

EXAMPLE 3

Re-186 Radiolabeling

In a typical run, a solution containing 880 micrograms of Sn(II) is mixed with a solution containing 1 mg of monoclonal anti-CEA intact antibody. Addition of $18.9 \times 10^{-11}$ mol rhenium-186, with an activity of 9 million cpm, as perrhenate in saline, followed by incubation for 1 hour at room temperature, gives a 75% incorporation of rhenium into the protein. The labeled antibody is stable to air oxidation and its immunoreactivity is high when measured on a CEA column. The solution can be used directly for in vivo injection.

EXAMPLE 4

Re-188 Radiolabeling

In a typical run, 1 mg of anti-CEA Fab'-SH (SH generated by reduction of F(ab')$_2$ with cysteine, mercaptoethanol or dithiothreitol), is placed in an argon atmosphere together with 1 ml of 100 mM tartrate+50 mM acetate buffer and an Sn(II) species containing about 123 ug of Sn(II). 20–2000 μl of a perrhenate solution, depending on concentration, equivalent to up to about $1 \times 10^{-9}$ mol rhenium is added. After mixing, the reaction is effected in 1 to 6 hours with rhenium incorporations of 60 to 100% seen. The solution of labeled antibody fragment can be used directly for in vivo injection.

In order to confirm the labeling efficiency, a sample of the labeled protein is immediately applied to an acrylamide column and eluted with either acetate buffer or saline. The labeled protein elutes with the void volume (approx. 5 ml) and is shown to be 100% protein-bound rhenium by ITLC in saline. The conjugates can be equally well purified by a quick run through a minicolumn using a syringe barrel, again to give a 100% protein bound label.

The labeled fragment passes through filters with as low as 0.05 micron pore size, showing lack of aggregate. In all column procedures and filtrations, essentially 100% recovery of radioactivity is obtained. Chromatography on HPLC and ITLC shows the radioactivity eluting/migrating with the protein fraction.

EXAMPLE 5

F(ab')$_2$-SH Production (a) Partial reduction of intact antibody

A solution of intact anti-lymphoma IgG 2A antibody in tris buffer (0.1 M, pH 8.7) between 10 and 20 mg/ml is made 25 millimolar in L-cysteine. After 10 minutes at 4 C it is purified by size-exclusion chromatography in 50 mM acetate, pH 4.5, and the combined protein fractions concentrated to 10 mg/μl. Analysis by the Ellman reaction shows approximately 3.5 SH groups per mole of IgG. Reduction can be effected by other thiol reducing agents, e.g., dithiothreitol (DTT), 2-mercaptoethanol (2-ME), metallothionein C-terminal hexpeptide (MCTP), and the like.

(b) Enzymatic digestion

Digestion of a sample of partially reduced anti-lymphoma antibody, produced according to part (a) above, is performed by adjustment of the pH to 4.0 with a little citric acid solution (1 M) and treatment of the IgG with pepsin (equivalent to a final concentration of 200 μg/ml) for 3–4 hours at 37° C. The course of the reaction is followed by size-exclusion HPLC and when all the intact IgG has disappeared the reaction is stopped by cooling to 4° C., raising the pH to 5.5, and immediately applying to a preparative HPLC column (Zorbax 250, DuPont) and collecting fractions every 12 seconds between 8 and 15 minutes retention time. Fractions eluting around 9.5 minutes are analyzed, and combined if found identical, prior to reconcentration. The F(ab')$_2$-SH thus produced is found to be one peak on HPLC with no evidence of monovalent Fab'. It is stored in a liquid nitrogen bath prior to radiolabelling.

EXAMPLE 6

Technetium-99m labeling

In a typical run, mg of partially reduced anti-lymphoma F(ab')$_2$-SH, produced according to Example 5, is placed in an argon atmosphere together with 1 ml of 10–100 mM tartrate+50 mM acetate buffer and an Sn(II) species containing about 120 μg of Sn(II). 20–2000 μl of a pertechnetate solution, depending on concentration, equivalent to up to about $1 \times 10^{-9}$ mol technetium is added. After only about 5 minutes, substantially 100% of the technetium label is bound to the F(ab')$_2$ fragment, with substantially no further fragmentation to Fab'.

The labeled fragment passes through filters with as low as 0.05 micron pore size, showing lack of aggregate. In all column procedures and filtrations, essentially 100% recovery of radioactivity is obtained. Chromatography on HPLC and ITLC shows the radioactivity eluting/migrating with the protein fraction. Labeled fragment is highly resistant to reoxidation in either acetate buffer or saline when exposed to the atmosphere for up to 72 hours. Thus, a technetium radiolabeled product can be ready for injection within a few minutes with minimal laboratory handling.

EXAMPLE 7

Rhenium-188 labeling

In a typical run, mg of partially reduced antilymphoma F(ab')$_2$-SH, produced according to Example 5, is placed in an argon atmosphere together with 1 ml of 10–100 mM tartrate+50 mM acetate buffer and an Sn(II) species containing about 120 μg of Sn(II). 20-2000 μl of a perrhenate solution, depending on concentration, equivalent to up to about $1 \times 10^{-9}$ mol rhenium is added. After mixing, the label may be left 1 to 18 hours with rhenium incorporations, by ITLC, of 60 to 95% seen. The resultant solution can be used as is for injection into a patient.

In order to evaluate radiolabeling efficiency, the labeled fragment is immediately applied to an acrylamide column and eluted with either acetate buffer or saline. The labeled protein elutes with the void volume (approx. 5 ml) and is shown to be 100% protein bound rhenium by ITLC in saline. The conjugates can be equally well purified by a quick run through a minincolumn using a syringe barrel, again to give a 100% protein bound label.

The label passes through filters with as low as 0.05 micron pore size, showing lack of aggregate. In all column procedures and filtrations, essentially 100% recovery of radioactivity is obtained. Chromatography on HPLC and ITLC shows the radioactivity eluting/migrating with the protein fraction. Labeled fragments are highly resistant to reoxidation in either acetate buffer or saline when exposed to the atmosphere for up to 72 hours. Thus, a rhenium labeled product can be ready for injection within a few hours at most, with minimal laboratory handling.

EXAMPLE 8

F(ab')$_2$-MCTP-SH Production (a) Antibody-MCTP conjugate

Mouse liver metallothionein-1 fragment (56-61), 6.2 mg ($1 \times 10^{-5}$ mol) (Sigma Chemical Company) is dissolved in 495 μl of phosphate buffer, ph 4.4, and treated with 10 μl of a 191 mg/ml solution of 1-ethyl-3(3-dimethylaminopropyl)-carbodiimide in phosphate buffer, pH 4.4. Care is taken to ensure a final reaction pH between 4.0 and 4.5 and the reaction is performed at 4° C. The reaction proceeds for 15 min.

An antibody solution of anti-CEA IgG, concentrated to 10-15 mg/ml in deoxygenated tris buffer, pH 8.7, is cooled to 4° and treated with the activated MCTP for 10 minutes at 4°. The reaction mixture is then immediately applied to an acrylamide column and the IgG fraction collected by elution with deoxygenated sodium acetate/saline buffer 50/150 mM, pH 4.5. Analysis by the Ellman reaction shows about 5-6 SH groups per antibody.

(b) Enzymatic digestion

The antibody-MCTP conjugate is fragmented using pepsin, analogously to Example 5(b). The digestion process is monitored by size exclusion HPLC and when the reaction mixture has fragmented to about 90% F(ab)'$_2$ (in approximately 1 hr) it is placed on ice and immediately purified by preparative size exclusion HPLC using an acetate buffer, at pH 4.5. Purified F(ab)'$_2$-MCTP fractions are collected, combined and an appropriate amount of stannous ion solution added. The resultant solutions are stored frozen, preferably in a liquid nitrogen bath.

EXAMPLE 9

Radiolabeling

The F(ab')$_2$-MCTP produced according to Example 8 can be radiolabeled with Tc-99m and radioisotopes of rhenium in the same fashion and by the same procedures as set forth in Examples 6 and 7 above for F(ab')$_2$-SH, with appropriate adjustment for the fact that the fragment/metallothionein conjugate generally contains more free thiol groups per fragment molecule than the partially reduced, digested antibody produced according to the procedure of Example 5.

It is convenient to use the single-vial preparation according to Example 8(b), containing both the F(ab')$_2$-MCTP and Sn(II), gently thawed and warmed to room temperature. Addition of pertechnetate in saline and reaction for about 5 minutes produces a solution of substantially 100% labeled F(ab')$_2$ ready for in vivo injection. Addition of perrhenate in saline and reaction for 1-18 hours produces a solution of 60-100% labeled F(ab')$_2$ ready for in vivo injection.

This is believed to be the only simple and highly efficient method now available for producing Tc-labeled and Re-labeled antibody F(ab')$_2$ fragments uncontaminated by Tc-Fab' and Re-Fab'.

The foregoing examples are merely illustrative and numerous variations and modifications can be effected by one of ordinary skill in the art to adapt the method, kit and uses thereof according to the invention to various usages and conditions without departing from the scope and spirit of the invention.

The broad scope of the invention is defined by the appended claims, and by the penumbra of equivalents thereof.

What is claimed is:

1. A method for producing an F(ab')$_2$ antibody fragment radiolabeled with Tc-99m or a radioisotope of rhenium, comprising the steps of:
   (a) partially reducing an intact antibody with a reducing agent for cleaving disulfide groups, in an amount sufficient to generate a plurality of proximal free sulfhydryl groups but insufficient to cleave or render immunologically inactive said antibody, and recovering partially reduced antibody;
   (b) cleaving said partially reduced antibody to generate a partially reduced F(ab')$_2$ fragment; and
   (c) contacting a solution of said partially reduced F(ab')$_2$ fragment with stannous ions, and then with radiopertechnetate or radioperrhenate, the amount of stannous ion being in excess over that required to substantially completely reduce said radiopertechnetate or radioperrhenate but not sufficient to precipitate the protein from said solution, and recovering radiolabeled F(ab')$_2$ substantially free of Fab' antibody fragment and aggregates.

2. The method of claim 1, wherein said antibody fragment specifically binds a tumor marker.

3. The method of claim 1, wherein said antibody fragment specifically binds an antigen associated with an infectious lesion, microorganism, parasite, myocardial infarction, clot, atherosclerotic plaque, or normal organ or tissue.

4. The method of claim 1, wherein said antibody fragment is radiolabeled with Tc-99m, the concentration of antibody fragment in said solution is about 0.01-10 mg/ml, and the amount of stannous ion is a about 0.1-50 μg/ml.

5. The method of claim 4, wherein the concentration of antibody fragment in said solution is about 0.1-5 mg/ml, and the amount of stannous ion is about 0.5-25 μg/ml.

6. The method of claim 4, wherein the amount of pertechnetate is about 2-50 mCi/mg of antibody fragment, and the time of reaction is about 0.1-10 min.

7. The method of claim 6, wherein the amount of pertechnetate is about 5-30 mCi/mg, and the time of reaction is about 1-5 min.

8. The method of claim 1, wherein said antibody fragment is radiolabeled with a radioisotope of rhenium, the radioisotope in the radioperrhenate is substantially carrier-free Re-188, the concentration of antibody fragment in said solution is about 1-20 mg/ml, and the amount of stannous ion is about 100-10,000 µg/ml.

9. The method of claim 8, wherein the concentration of antibody fragment in said solution is about 10-20 mg/ml, and the amount of stannous ion is about 500-5,000 µg/ml.

10. The method of claim 8, wherein the amount of perrhenate is about 10-500 mCi, and the time of reaction is about 1 min-4 hr.

11. The method of claim 10, wherein the amount of perrhenate is about 50-250 mCi, and the time of reaction is about 15 min-2 hr.

12. The method of claim 1, wherein said antibody fragment is radiolabeled with a radioisotope of rhenium, the radioisotope in the radioperrhenate is carrier-added Re-186, the concentration of antibody fragment in said solution is about 1-20 mg/ml, and the amount of stannous ion is about 1-1,000 mg/ml.

13. The method of claim 12, wherein the concentration of antibody fragment in said solution is about 10-20 mg/ml, and the amount of stannous ion is about 5-500 mg/ml.

14. The method of claim 12, wherein the amount of perrhenate is about 10-500 mCi, and the reaction is about 1 min-2 hr.

15. The method of claim 14, wherein the amount of perrhenate is about 50-250 mCi, and the time of reaction is about 15 min-2 hr.

16. The method of claim 1, wherein said antibody fragment is labeled with Tc-99m and said method yields substantially 100% incorporation of said Tc-99m.

17. A method for producing an F(ab')$_2$ antibody fragment radiolabeled with Tc-99 m or a radioisotope of rhenium, comprising the steps of:
  (a) conjugating an intact antibody with an addend containing a plurality of proximal free sulfhydryl groups, and recovering resultant antibody conjugate containing a plurality of proximal free sulfhydryl groups;
  (b) cleaving said antibody conjugate to generate an F(ab')$_2$ fragment conjugate containing a plurality of proximal free sulfhydryl groups; and
  (c) contacting a solution of F(ab')$_2$ fragment conjugate containing a plurality of proximal free sulfhydryl groups with stannous ions, and then with radiopertechnetate or radioperrhenate, the amount of stannous ion being in excess over that required to substantially completely reduce said radiopertechnetate or radioperrhenate but not sufficient to precipitate the protein from said solution, and recovering radiolabeled F(ab')$_2$ substantially free of Fab' antibody fragments and aggregates.

18. The method of claim 17, wherein said antibody fragment specifically binds a tumor marker.

19. The method of claim 17, wherein said antibody fragment specifically binds an antigen associated with an infectious lesion, microorganism, parasite, myocardial infarction, clot, atherosclerotic plaque, or normal organ or tissue.

20. The method of claim 19, wherein the amount of perrhenate is about 10-500 mCi, and the time of reaction is about 1 min-4 hr.

21. The method of claim 20, wherein the amount of perrhenate is about 50-250 mCi, and the time of reaction is about 15 min-2 hr.

22. The method of claim 17, wherein said antibody fragment conjugate is radiolabeled with a radioisotope of rhenium, the radioisotope in the radioperrhenate is substantially carrier-free Re-188, the concentration of antibody fragment conjugate in said solution is about 1-20 mg/ml, and the amount of stannous ion is about 100-10,000 µg/ml.

23. The method of claim 22, wherein the concentration of antibody fragment conjugate in said solution is about 10-20 mg/ml, and the amount of stannous ion is about 500-5,000 µg/ml.

24. The method of claim 17, wherein said antibody fragment conjugate is radiolabeled with a radioisotope of rhenium, the radioisotope in the radioperrhenate is carrier-added Re-186, the concentration of antibody fragment conjugate in said solution is about 1-20 mg/ml, and the amount of stannous ion is about 1-1,000 mg/ml.

25. The method of claim 17, wherein the concentration of antibody fragment conjugate in said solution is about 10-20 mg/ml, and the amount of stannous ion is about 5-500 mg/ml.

26. The method of claim 24, wherein the amount of perrhenate is about 10-500 mCi, and the time of reaction is about 1 min-4 hr.

27. The method of claim 26, wherein the amount of perrhenate is about 50-250 mCi, and the time of reaction is about 15 min-2 hr.

28. The method of claim 17, wherein said antibody fragment conjugate is radiolabeled with Tc-99m, the concentration of antibody fragment conjugate in said solution is about 0.01-10 mg/ml, and the amount of stannous ion is about 0.1-50 µg/ml.

29. The method of claim 28, wherein the concentration of antibody fragment conjugate in said solution is about 0.1-5 mg/ml, and the amount of stannous ion is about 0.5-25 µg/ml.

30. The method of claim 28, wherein the amount of pertechnetate is about 2-50 mCi/mg of antibody fragment conjugate, and the time of reaction is about 0.1-10 min.

31. The method of claim 30, wherein the amount of pertechnetate is about 5-30 mCi/mg/ and the time of reaction is about 1-5 min.

32. The method of claim 17, wherein said antibody fragment is labeled with Tc-99m and said method yields substantially 100% incorporation of said Tc-99m.

33. In a method of imaging a tumor, an infectious lesion, a myocardial infarction, a clot, atherosclerotic plaque, or a normal organ or tissue, wherein an antibody fragment which specifically binds to an antigen produced by or associated with said tumor, infectious lesion, myocardial infarction, clot, atherosclerotic plaque, or normal organ or tissue, and radiolabeled with a pharmaceutically inert radioisotope capable of external detection, is parenterally injected into a human patient and, after a sufficient time for said radiolabeled antibody or antibody fragment to localize and for non-target background to clear, the site or sites of accretion of said radiolabeled antibody fragment are detected by an external imaging camera, the improvement wherein said radiolabeled antibody fragment is a Tc-99m-labeled F(ab')$_2$ antibody fragment made according to the method of claim 1.

34. The method of claim 33, wherein said antibody fragment is labeled with Tc-99m and said method yields substantially 100% incorporation of said Tc-99m.

35. The method of claim 33, wherein said radiolabeled antibody fragment is injected without removal of the reducing agent.

36. In a method of imaging a tumor, an infectious lesion, a myocardial infarction, a clot, atherosclerotic plaque, or a normal organ or tissue, wherein an antibody fragment which specifically binds to an antigen produced by or associated with said tumor, infectious lesion, myocardial infarction, clot, atherosclerotic plaque, or normal organ or tissue, and radiolabeled with a pharmaceutically inert radioisotope capable of external detection, is parenterally injected into a human patient and, after a sufficient time for said radiolabeled antibody or antibody fragment to localize and for non-target background to clear, the site or sites of accretion of said radiolabeled antibody fragment are detected by an external imaging camera, the improvement wherein said radiolabeled antibody fragment is a Tc-99m-labeled F(ab')$_2$ antibody fragment made according to the method of claim 17.

37. The method of claim 36, wherein said antibody fragment is labeled with Tc-99m and said method yields substantially 100% incorporation of said Tc-99m.

38. The method of claim 36, wherein said radiolabeled antibody fragment is injected without removal of the reducing agent.

39. The method of radioantibody therapy of a patient suffering from a tumor or an infectious lesion, wherein an antibody fragment which specifically binds to an antigen produced by or associated with a tumor or an infectious lesion, and radiolabeled with a therapeutically effective radioisotope, is parenterally injected into a human patient suffering from said tumor or infectious lesion, the improvement wherein said radiolabeled antibody fragment is a rhenium radiolabeled F(ab')$_2$ antibody fragment made according to the method of claim 1.

40. The method of claim 39, wherein said radiolabeled antibody fragment is injected without removal of the reducing agent.

41. In a method of radioantibody therapy of a patient suffering from a tumor or an infectious lesion, wherein an antibody fragment which specifically binds to an antigen produced by or associated with a tumor or an infectious lesion, and radiolabeled with a therapeutically effective radioisotope, is parenterally injected into a human patient suffering from said tumor or infectious lesion, the improvement wherein said radiolabeled antibody fragment is a rhenium radiolabeled F(ab')$_2$ antibody fragment made according to the method of claim 17.

42. The method of claim 41, wherein said radiolabeled antibody fragment is injected without removal of the reducing agent.

43. A kit for radiolabeling an F(ab')$_2$ antibody fragment conjugate with the Tc-99m radioisotope of technetium, consisting essentially of, in a suitable container, about 0.01-10 mg per unit dose of an F(ab')$_2$ antibody fragment conjugate and which contains a plurality of adjacent free sulfhydryl groups; and about 0.1-50 μg per unit dose of stannous ions; wherein said F(ab')$_2$ antibody fragment conjugate is prepared by a process comprising the steps of:

(a) conjugating an intact antibody with an addend containing a plurality of proximal free sulfhydryl groups, and recovering resultant antibody conjugate containing a plurality of proximal free sulfhydryl groups; and (b) cleaving said antibody conjugate to generate an F(ab')$_2$ fragment conjugate containing a plurality of proximal free sulfhydryl groups.

44. A kit for radiolabeling an F(ab')$_2$ antibody fragment conjugate with the substantially carrier-free Re-188 radioisotope of rhenium, consisting essentially of, in a suitable container, about 1-20 mg per unit does of an F(ab')$_2$ antibody fragment conjugate and which contains a plurality of proximal free sulfhydryl groups; and about 100-10,000 μg per unit dose of stannous ions; wherein said F(ab')$_2$ antibody fragment conjugate is prepared by a process comprising the steps of:

(a) conjugating an intact antibody with an addend containing a plurality of proximal free sulfhydryl groups, and recovering resultant antibody conjugate containing a plurality of proximal free sulfhydryl groups; and (b) cleaving said antibody conjugate to generate an F(ab')$_2$ fragment conjugate containing a plurality of proximal free sulfhydryl groups.

45. A kit for radiolabeling an antibody fragment with the carrier-added Re-186 radioisotope of rhenium, consisting essentially of, in a suitable container, about 1-20 mg per unit dose of an F(ab')2 antibody fragment conjugate which contains a plurality of adjacent free sulfhydryl groups; and about 1-1,000 mg per unit dose of stannous ions; wherein said F(ab')$_2$ antibody fragment conjugate is prepared by a process comprising the steps of:

(a) conjugating an intact antibody with an addend containing a plurality of proximal free sulfhydryl groups, and recovering resultant antibody conjugate containing a plurality of proximal free sulfhydryl groups; and (b) cleaving said antibody conjugate to generate an F(ab')$_2$ fragment conjugate containing a plurality of proximal free sulfhydryl groups.

46. A kit for radiolabeling an F(ab')$_2$ antibody fragment with the Tc-99m radioisotope of technetium, consisting essentially, in a suitable container, about 0.1-10 mg per unit does of an F(ab')$_2$ antibody fragment, and which contains a plurality of adjacent free sulfhydryl groups; and about 0.1-50 μg per unit dose of stannous ions; wherein said F(ab')$_2$ antibody fragment is prepared by a process comprising the steps of:

(a) partially reducing an intact antibody with a reducing agent for cleaving disulfide groups, in an amount sufficient to generate a plurality of proximal free sulfhydryl groups but insufficient to cleave or render immunologically inactive said antibody, and recovering partially reduced antibody;

(b) cleaving said partially reduced antibody to generate a partially reduced F(ab')$_2$ fragment.

47. A kit for radiolabeling an F(ab')$_2$ antibody fragment with the substantially carrier-free Re-188 radioisotope of rhenium, consisting essentially of, in a suitable container, about 1-20 mg per unit dose of an F(ab')$_2$ antibody fragment, and which contains a plurality of proximal free sulfhydryl groups; and about 100-10,000 μg per unit dose of stannous ions; wherein said F(ab')2 antibody fragment is prepared by a process comprising the steps of:

(s) partially reducing an intact antibody with a reducing agent for cleaving disulfide groups, in an amount sufficient to generate a plurality of proximal free sulfhydryl groups but insufficient to cleave or render immunologically inactive said antibody, and recovering partially reduced antibody;

(b) cleaving said partially reduced antibody to generate a partially reduced F(ab')2 fragment.

48. A kit for radiolabeling an antibody or antibody fragment with the carrier-added Re-186 radioisotope of rhenium, consisting essentially of, in a suitable container, about 1-20 mg per unit does of an F(ab')2 antibody fragment, and which contains a plurality of adjacent free sulfhydryl groups; and about 1-1,000 mg per unit dose of stannous ions; wherein said F(ab')2 antibody fragment is prepared by a process comprising the steps of:

(a) partially reducing an intact antibody with a reducing agent for cleaving disulfide groups, in an amount sufficient to generate a plurality of proximal free sulfhydryl groups but insufficient to cleave or render immunologically active said antibody, and recovering partially reduced antibody;

(b) cleaning said partially reduced antibody to generate a partially reduced F(ab')2 fragment.

* * * * *